(12) United States Patent  (10) Patent No.: US 8,440,842 B2
Moellmann et al.  (45) Date of Patent: May 14, 2013

(54) ANTIMICROBIAL COMPOUNDS, THEIR SYNTHESIS AND THEIR USE FOR TREATMENT OF MAMMALIAN INFECTIONS

(75) Inventors: Ute Moellmann, Jena (DE); Vadim Makarov, Moscow (RU); Cole T. Stewart, Ecublens (CH)

(73) Assignee: Leibniz-Institut fuer Naturstoff-Forschung und Infektionsbiologie e.V. Hans-Knoell-Institut, Jena (DE)

( * ) Notice: Subject to any disclaimer, the term of this patent is extended or adjusted under 35 U.S.C. 154(b) by 316 days.

(21) Appl. No.: 12/669,748

(22) PCT Filed: Jun. 25, 2008

(86) PCT No.: PCT/EP2008/005142
§ 371 (c)(1),
(2), (4) Date: Jul. 22, 2010

(87) PCT Pub. No.: WO2009/010163
PCT Pub. Date: Jan. 22, 2009

(65) Prior Publication Data
US 2010/0286130 A1    Nov. 11, 2010

(30) Foreign Application Priority Data
Jul. 16, 2007 (EP) .................................. 07013899

(51) Int. Cl.
*A61K 31/54* (2006.01)
*C07D 327/06* (2006.01)
*C07D 409/00* (2006.01)

(52) U.S. Cl.
USPC ............... 549/15; 549/14; 549/23; 514/224.2

(58) Field of Classification Search .......................... None
See application file for complete search history.

(56) References Cited

U.S. PATENT DOCUMENTS
3,522,247 A    7/1970    Cronin

FOREIGN PATENT DOCUMENTS
EP    1 568 697    8/2005
EP    1568697 A1 *    8/2005
WO    WO-2005/092872    10/2005
WO    WO-2007/134625    11/2007
WO    WO 2007134625 A1 *    11/2007

OTHER PUBLICATIONS

Ceraulo et al., Studies in organic mass spectrometry. I. Electron impact-induced fragmentation of 2-substituted 4H-1,3-benzothiazin-4-ones, Annali di Chimica (Rome, Italy) (1977), 67(9-12), 707-19, ISSN: 0003-4592, STN document No. 93:167097.*
Palazzo et al., Reaction of 2H-1,3-benzothiazin-2-thione-4(3H)-one with primary amines, Atti della Accademia di Scienze Letter e Arti di Palermo, Parte 1: Scienze (1974), Volume Date 1973, 33(2), 411-20, STN document number 83:114317.*
English Abstract of Antituberculous substances, C.V. Gheorghiu, et al.; "Rev. chim., Acad. rep.populaireRoumaine 1", No. 1, 97-125 (1956) XP-002958704.

* cited by examiner

*Primary Examiner* — Shengjun Wang
*Assistant Examiner* — Svetlana M Ivanova
(74) *Attorney, Agent, or Firm* — Swanson & Bratschun, L.L.C.

(57) ABSTRACT

The present invention relates to compounds of Formula (I)

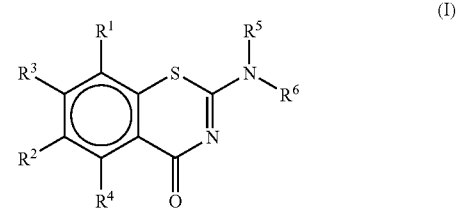

or salts thereof wherein $R^1$, $R^2$, $R^3$, $R^4$, $R^5$, $R^6$, and other variables enumerated under one or more of same are as defined herein. Compounds of Formula I have activity as antimicrobial agents. Also disclosed are pharmaceutical compositions and methods of treating and preventing microbial infections in mammals, for example, a tuberculosis or leprosy infection, which employ compounds of Formula (I) or salts thereof.

10 Claims, No Drawings

ANTIMICROBIAL COMPOUNDS, THEIR SYNTHESIS AND THEIR USE FOR TREATMENT OF MAMMALIAN INFECTIONS

BACKGROUND OF THE INVENTION

The present invention relates to novel benzothiazin derivatives and their use as antibacterial agents in infectious diseases of mammals (humans and animals) caused by bacteria, especially diseases like tuberculosis (TB) and leprosy caused by mycobacteria.

Thiazinone, their derivatives and their use as antibacterial agents, especially against mycobacteria (TB), laid open for public in AR 24 25 67 A1, AU 37 04 400 A1, CA 13 22 551 C1 or EP 0 245 901 B1 for instance.

As known, there is a threatening worldwide increase in tuberculosis infections with mycobacteria which developed resistance against the available therapeutics (B. R. Bloom, J. L. Murray, Tuberculosis: commentary on a reemergent killer. Science 1992, 257, 1055-1064). Extremely dangerous is the development of multidrug resistant (MDR) mycobacteria. These are mycobacteria, resistant at least against two of the most active tuberculosis drugs, isoniazid and rifampicin, but also against streptomycin, pyranzinamid and ethambutol. The proportion of MDR-TB in some countries is already more than 20%. Even more threatening became the situation since the first cases of XDR-TB (extremly resistant TB) were diagnosed last year in South Africa. Now XDR-TB is already spread over all continents. Mycobacteria causing XDR-TB are resistant against the first line TB drugs Rifampicin, Isoniazid, Pyrazinamid, Ethambutol and additionally against the second line chinolones and aminoglycosides. (Nature Med. 2007, 13, 295-298) Together with the increased number of TB diseases generally, worldwide it causes about 2,000,000 deaths annually.

For the treatment of such diseases, like (TB) or leprosy, there is an urgent need for new drugs with new mechanisms of actions, especially to overcome drug resistance and to overcome the known dramatic side effects of the available drugs.

SUMMARY OF THE INVENTION

The present invention aims at the generation of new compounds with activity against mycobacteria as potential new tuberculosis drugs to overcome problems concerning resistance and drug intolerance.

This aim has been solved by providing compounds of the formula I

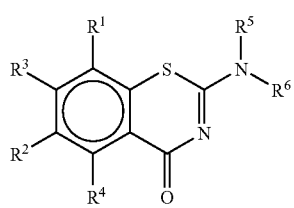

wherein $R^1$ and $R^2$ are, independently of each other, $NO_2$, $NR^7R^8$, $NHOR^9$, $COOR^9$, $CN$, $CONR^{10}R^{11}$, $CHO$, $F$, $Cl$, $Br$, $SO_2NR^{12}R^{13}$, lower alkoxy, $OCF_3$, mono-, di or trifluoromethyl;

$R^3$ and $R^4$ are, independently of each other, H, a saturated or unsaturated, linear or branched aliphatic radical having 1-3 chain members, F, Cl, Br, lower alkoxy;

$R^5$ is H, a saturated or unsaturated, halogenated or unhalogenated, linear or branched aliphatic radical having 1-7 chain members;

$R^6$ is a radical:

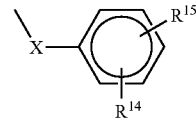

wherein X is saturated or unsaturated, halogenated or unhalogenated, linear or branched aliphatic radical having 1-5 chain members, or $R^5$ and $R^6$ together represent bivalent radicals wherein n is 1-4:

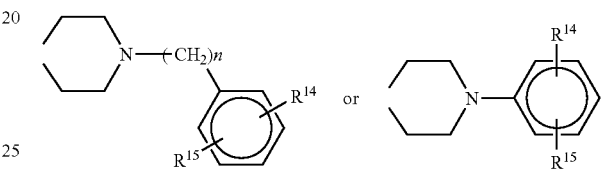

$R^7$-$R^{13}$ are, independently of each other H or a saturated or unsaturated, halogenated or unhalogenated, linear or branched aliphatic radical having 1-5 chain members, phenyl, benzyl or $R^7$ and $R^8$ together, $R^{10}$ and $R^{11}$ together, $R^{12}$ and $R^{13}$ together represent a linear or branched aliphatic bivalent radical having 1-7 chain members;

$R^{14}$ and $R^{15}$ are, independently of each other, H, linear or branched aliphatic radical having 1-5 chain members, F, Cl, Br, $NO_2$, $NH_2$, $CF_3$.

DETAILED DESCRIPTION OF THE INVENTION

In a preferred embodiment the invention concerns compounds of the formula (I) selected from the group consisting of 2-[4-(2-$R^{14}$,5-$R^{15}$-phenyl)piperazin-1-yl]-8-nitro-6-(trifluoromethyl)-4H-1,3-benzothiazin-4-one, 2-[4-(2-$R^{14}$,6-$R^{15}$-phenyl)piperazin-1-yl]-8-nitro-6-(trifluoromethyl)-4H-1,3-benzothiazin-4-one, 2-[4-(3-$R^{14}$,5-$R^{15}$-phenyl)piperazin-1-yl]-8-nitro-6-(trifluoromethyl)-4H-1,3-benzothiazin-4-one, 2-[benzyl(methyl)amino]-8-nitro-6-$R^2$-4H-1,3-benzothiazin-4-one, 2-[benzyl($R^5$)amino]-8-nitro-6-(trifluoromethyl)-4H-1,3-benzothiazin-4-one, 2-[benzyl($R^5$)amino]-8-nitro-6-$R^2$-4H-1,3-benzothiazin-4-one, 2-[benzyl($R^5$)amino]-8-nitro-6-chloro-4H-1,3-benzothiazin-4-one, 2-[benzyl($R^5$)amino]-8-nitro-6-fluoro-4H-1,3-benzothiazin-4-one, 2-[benzyl($R^5$)amino]-8-$R^1$-6-(trifluoromethyl)-4H-1,3-benzothiazin-4-one, wherein $R^1$, $R^5$, $R^{14}$ and $R^{15}$ have the above meanings. The present invention is even more particularly concerned with at least one compound selected from the group consisting of 2-[4-(4-Chlorophenyl)piperazin-1-yl]-6,8-dinitro-4H-1,3-benzothiazin-4-one, 2-[4-(5-chloro-2-methylphenyl)piperazin-1-yl]-8-nitro-6-(trifluoromethyl)-4H-1,3-benzothiazin-4-one, 8-Nitro-6-(trifluoromethyl)-2-{4-[3-(trifluoromethyl)phenyl]piperazin-1-yl}-4H-1,3-benzothiazin-4-one,
2-[Benzyl(ethyl)amino]-8-nitro-6-(trifluoromethyl)-4H-1,3-benzothiazin-4-one,
2-[Benzyl(methyl)amino]-8-nitro-6-(trifluoromethyl)-4H-1,3-benzothiazin-4-one,
2-[4-(2-Fluorophenyl)piperazin-1-yl]-8-nitro-6-(trifluoromethyl)-4H-1,3-benzothiazin-4-one,
2-(4-Benzylpiperazin-1-yl)-8-nitro-6-(trifluoromethyl)-4H-1,3-benzothiazin-4-one,
2-(Benzylamino)-8-nitro-6-(trifluoromethyl)-4H-1,3-benzothiazin-4-one,
2-{Methyl[(1R)-1-phenylethyl]amino}-8-nitro-6-(trifluoromethyl)-4H-1,3-benzothiazin-4-one,
2-[Benzyl(methyl)amino]-6-chloro-8-nitro-4H-1,3-benzothiazin-4-one.

We used 4 different methods for the synthesis of new and novel 1,3-benzothiazin-4-one derivatives. Methods A, B and C propose to use as starting material well known polysubstituted 2-chloro(bromo)-benzcarboxamides, many of them described in the literature or can be easily prepared by analogues methods (Isaew S. G. *Farm. Zh.* (Kiev), 2000, 52; Makosza M., Nizamov S. *Org. Prep. and Proced. Int.*, 1997, 29, 707; Nerin C., Torres A. R., Domento C., Cacho J. *J. Agr. and Food Chem.*, 1996, 44, 4009; Thiel W., Mayer R., Jauer E.-A., Modrow H., Dost H. *J. Prakt. Chem.*, 1986, 328, 497; Yokoyama M., Yoshida S., Imamoto T. *Synthesis*, 1982, 591; Romanowski J., Eckstein Z. *Pol. J. Chem.*, 1984, 58, 263; Nisato D., Sacilotto R., Frigerio M., Boveri S., Palmisano G., Lesma G. *Org. Prep. Proced. Int:*, 1985, 17, 75; Oikawa N., Nakagawa Y., Nishimura K., Ueno T., Fujita T., *Pestic. Sci.*, 1994, 41, 139; Welch D. E., Baron R. R., *J. Med. Chem.*, 1969, 12, 299; Fuller R. W., Molloy B. B., Day W. A., Roush B. W., March M. M., *J. Med. Chem.*, 1973, 16, 101 and many others).

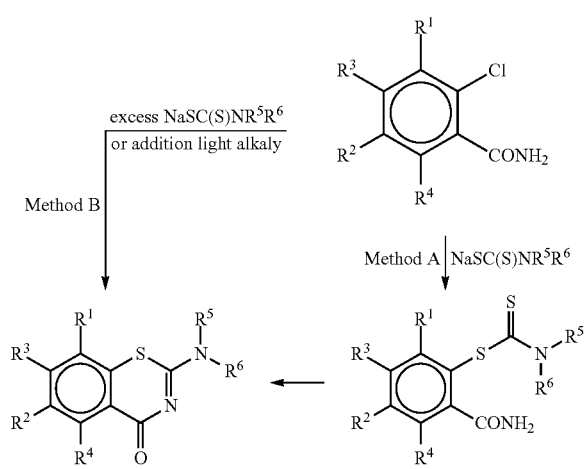

Method A

The starting 2-chlorobenzcarboxamides were treated by 1,0-1,2 equimolar quantity of the metal salts of dithiocarbamates in alcohols, aceton or in their mixture under 0-50° C. for a period of about one quarter of an hour to about 24 hours. Preferably, this reaction is conducted in alcohol at room temperature. The reaction mixture was diluted by water and solid 2-dithiocarbamoylbenzcarboxamide was filtered off. For the next step it is possible to use crude product or to recrystallize it from a suitable organic solvent. 2-Dithiocarbamoylbenzcarboxamide was treated by light alkaly (e.g. $Na_2HPO_4$, $NaHCO_3$, $Na_2CO_3$, etc) in water, alcohols or in a mixture of water/alcohol at a temperature of 50-100° C. for 2-36 hours. Preferably, this reaction is conducted in a mixture of water/alcohol at 50-75° C. for about 24 hours. When the reaction is complete, the 2-substituted-4H-1,3-benzothiazin-4-one is obtained by conventional recovery procedures, e.g. trituration with ethylacetate or dilution with water, filtration and recrystallization from a suitable organic solvent.

Method B

This method proposes to use excess of metal dithiocarbamate as light alkaly in the benzothiazinone cyclization and not to isolate 2-dithiocarbamoylbenzcarboxamide. So, the starting 2-chlorobenzcarboxamides can be treated with a 1,2-2,5 equimolar quantity of the metal salts of dithiocarbamates in alcohols, aceton or in their mixture at 20-80° C. for a period of about 3-36 hours. Preferably, this reaction is conducted in alcohol or in a mixture of water/alcohol at 50-75° C. for about 24 hours. The aimed 2-substituted-4H-1,3-benzothiazin-4-one is obtained by recovery procedures from method A.

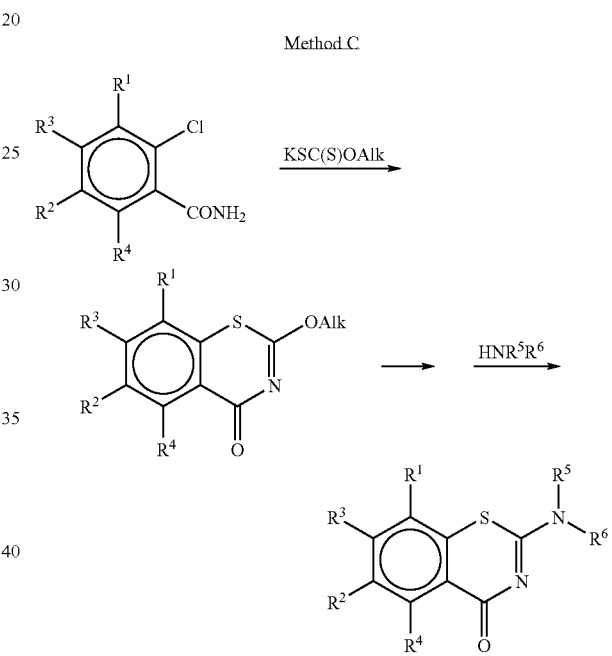

Method C

This method uses as starting material 2-chlorobenzencarboxamides. These compounds were treated with 1,1-2,0 fold excess of metal salts of allcylxantogenate, for example commercial available potassium ethylxantogenate, at a temperature of 20-100° C. in different alcohols, acetone, acetonitrile or other suitable organic solvents for a period of about one half hour to about 24 hours. Preferably, this reaction is conducted in alcohol at room temperature for about 24 hours. The isolated 2-alkoxy-4H-1,3-benzothiazin-4-one was treated with the corresponding amine $HNR^5R^6$ in acetic acid, alcohols, ethylacetate, DMF, aceton or acetonitril for a period of up to 48 hours for full exchange of the alkoxy group to the corresponding amine. After the process is completed the reaction mixture can be evaporated and diluted by water or it can be diluted by water directly. The aimed 2-$NR^5R^6$-4H-1,3-benzothiazin-4-one is recovered by customary isolation procedures, e.g. filtration and recrystallization from a suitable organic solvent.

Method D

The classical method of 1,3-benzothiazin-4-one synthesis by use of the reaction of thiocyanate salts with 2-chloroarylchloroanhydride and a subsequent treatment of the reaction mass with the corresponding amine is usable too. This method is well described in the scientific literature, for example: J. Imrich, P. Kristian, *Coll. Czech. Chem. Commun.*, 1982, 47, 3268-3282; D. Koscik, P. Kristian, J. Gonda, E. Dandarova, *Coll. Czech. Chem. Commun.*, 1983, 48, 3315-3328; D. Koscik, P. Kristian, O. Forgac, *Coll. Czech. Chem. Commun.*, 1983, 48, 3427-3432; T. H. Cronin, H.-J. E. Hess, U.S. Pat. No. 3,522,247.

Surprisingly the compounds of the invention exhibit strong antibacterial activity, especially against mycobacteria with minimal inhibitory concentrations (MIC) in the range of <0.000012-0.78 μg/ml for fast growing mycobacteria, of <0.39-3.12 μg/ml for *M. tuberculosis*, including multiresistant strains, determined by the classical method and of 2.0-50.0 ng/ml for *M. tuberculosis* H37Rv determined by the Alamar Blue method. Surprisingly the compounds of the invention demonstrate a high level of selectivity for mycobacteria only which reduces the potential for adverse side effects dramatically.

The compounds of the invention are non-mutagenic at 5 mg/ml in the SOS chromotest (M. Isidori, M. Lavorgna, A. Nardelli, L. Pascarella, A. Parella, *Sci. Total Environ.*, 2005, 346, 87-98; M. Bombardier, N. Bermingham, R. Legault, A. Fouquet, *Chemosphere*, 2001, 42, 931-44; D. A. Widdick, D. I. Edwards, *Mutat. Res.*, 1991, 259, 89-93).

Thus, the compounds of the invention are useful for the treatment of tuberculosis infections and other mycobacterial infections, in humans and in animals.

Accordingly, the invention concerns pharmaceutical compositions comprising a compound of the formula I.

The invention relates furthermore to a compound of the formula I for use in a method for the treatment of bacterial infections in mammals.

Preferred compounds of the formula I for use in such method are those specifically listed above.

The compounds of the invention are formulated for use by preparing a diluted solution or suspension in pharmaceutically acceptable aqueous, organic or aqueous-organic medium for topical or parenteral administration by intravenous, subcutaneous or intramuscular injection, or for intranasal application; or are prepared in tablet, capsule or aqueous suspension form with conventional excipients for oral administration or as suppositorium.

The compounds can be used in dosages from 0.001-1000 mg/kg body weight.

The examples which follow in the subsequent experimental part serve to is illustrate the invention but should not be construed as a limitation thereof.

The structures of the compounds of the invention were established by modes of synthesis and elementary analysis, and by nuclear magnetic resonance and mass spectra.

Embodiments

Starting Materials

Chemicals and solvents were purchased from Alfa-Aesar (GB) or from Aldrich Co. (Sigma-Aldrich Company, St-Louis, US) and were used in the synthesis without additional purification. Melting points were determined according to the BP procedure and are uncorrected (Electrothermal 9001, GB). If analyses are indicated only by the symbols of the elements, analytical results are within ±0.3% of the theoretical values (Carlo-Erba 5500, Italy). NMR spectra were determined with a Varian Unity Plus 400 (USA). Shifts for $^1$H NMR are reported in ppm downfield from TMS (δ). Mass spectra were obtained using a Finnigan SSQ-700 (USA) instrument with direct injection. Reactions and purity of compounds were controlled by TLC using Silicagel 60 $F_{254}$ aluminium sheets (Merck Co, Germany).

Example 1

2-[4-(4-Chlorophenyl)piperazin-1-yl]-6,8-dinitro-4H-1,3-benzothiazin-4-one, (compound 1)

0.5 g of 2-chloro-3,5-dinitrobenzcarboxamide was dissolved in 25 ml ethanol. The reaction mixture was treated with of 0.39 g of 4-(4-chlorophenyl)-piperazine dithiocarbamate sodium salt dihydrate and stored for 6 h at room temperature. The reaction mixture was poured into 50 ml of cooled water and the resulting yellow precipitate was filtered off. Pure final product was obtained after recrystallization from ethanol. 2-Aminocarbonyl-4,6-dinitrophenyl-4-(4-chlorophenyl)piperazine-1-carbodithioate is a light yellow crystalline solid. Yield 68%. mp 178-180° C. MS m/z 481 (M$^+$).

Anal. Calcd. for $C_{18}H_{16}ClN_5O_5S_2$: C, 44.86; H, 3.35; N, 14.53; S, 13.31.

Found: C, 44.71; H, 3.36; N, 14.62; S, 13.35.

0.5 g of 2-aminocarbonyl-4,6-dinitrophenyl-4-(4-chlorophenyl)piperazine-1-carbodithioate was dissolved in 25 ml ethanol. The reaction mixture was treated with of 0.2 g of $Na_2HPO_4 \times 12H_2O$ and refluxed for 6 h. Reaction mixture was cooled in the refrigerator and the light yellow precipitate was filtered off and washed with 50 ml water and 30 ml methanol. Pure final product was obtained after recrystallization twice from ethanol. 2-(1,4-2-[4-(4-Chlorophenyl)piperazin-1-yl]-6,8-dinitro-4H-1,3-benzothiazin-4-one is a light yellow crystalline solid. Yield 38%. mp 279-281° C. (EtOH)

MS m/z 447 (M$^+$).

$^1$H NMR (DMSO-$d_6$/CDCl$_3$) δ 9.08 and 8.95 (two 1H, two s, 2CH), 6.88 and 6.71 (two 2H, d, $C_6H_4Cl$), 3.68 and 3.30 (two 4H, m, N(CH$_2$CH$_2$)$_2$N) ppm.

Anal. Calcd. for $C_{18}H_{14}ClN_5O_5S$: C, 48.27; H, 3.15; N, 15.04; S, 7.16.

Found: C, 48.34; H, 3.22; N, 14.97; S, 7.23.

Example 2

2-[4-(5-chloro-2-methylphenyl)piperazin-1-yl]-8-nitro-6-(trifluoromethyl)-4H-1,3-benzothiazin-4-one, (compound 2)

Following the procedure of Example 1 using of 2-chloro-3-nitro-5-trifluoromethylbenzcarboxamide as starting material. Light yellow crystalline solid. Yield 44%. mp 158-161° C. (DMF/water)

MS m/z 484 (M$^+$).

$^1$H NMR (DMSO-$d_6$/CDCl$_3$) δ 8.80 and 8.77 (two 1H, two s, 2CH), 7.32 (1H, s, CH), 9.95 and 6.73 (two 1H, d, two CH), 3.65 and 3.29 (two 4H, m, N(CH$_2$CH$_2$)$_2$N), 2.29 (3H, s, CH$_3$) ppm.

Anal. Calcd. for $C_{20}H_{16}ClF_3N_4O_3S$: C, 49.54; H, 3.33; N, 11.55; S, 6.61.

Found: C, 49.45; H, 3.40; N, 11.47; S, 6.83.

Example 3

8-Nitro-6-(trifluoromethyl)-2-{4-[3-(trifluoromethyl) phenyl]piperazin-1-yl}-4H-1,3-benzothiazin-4-one, (compound 3)

Following the procedure of Example 1 using of 2-chloro-3-nitro-5-trifluoromethylbenzcarboxamide as starting material. Light yellow crystaline solid. Yield 33%. mp 201-203° C. (EtOH).

MS m/z 504 (M$^+$).

$^1$H NMR (DMSO-d$_6$/CDCl$_3$) δ 8.80 and 8.77 (two 1H, two s, 2CH), 7.61 (1H, s, CH), 7.39 and 7.03 (two 1H, d, two CH), 3.66 and 3.31 (two 4H, m, N(CH$_2$CH$_2$)$_2$N) ppm.

Anal. Calcd. for C$_{20}$H$_{14}$F$_6$N$_4$O$_3$S: C, 47.62; H, 2.80; N, 11.11; S, 6.36.

Found: C, 47.74; H, 2.91; N, 11.29; S, 6.53.

Example 4

2-[Benzyl(ethyl)amino]-8-nitro-6-(trifluoromethyl)-4H-1,3-benzothiazin-4-one, (compound 4)

A suspension of 1.2 g 2-chloro-3-amino-5-trifluoromethylbenzcarboxamide in 45 ml ethanol was treated with 2.0 g of benzyl(ethyl)dithiocarbamate sodium salt dihydrate and refluxed for 14 h. The dark red reaction mixture was diluted with 70 ml of water, cooled in the refrigerator for 6 hours, the light yellow precipitate was filtered off and washed with 50 ml ester. Pure final product was obtained after column chromatography (hexane/aceton 3:1). 2-[Benzyl(ethyl)amino]-8-nitro-6-(trifluoromethyl)-4H-1,3-benzothiazin-4-one is a light yellow crystalline solid. Yield 40%. mp 94-97° C.

MS m/z 409 (M$^+$).

$^1$H NMR (DMSO-d$_6$/CDCl$_3$) δ 8.80 and 8.77 (two 1H, two s, 2CH), 7.41-7.25 (5H, m, C$_6$H$_5$), 4.62 (2H, s, CH$_2$), 3.43 (2H, q, CH$_2$), 1.01 (3H, t, CH$_3$) ppm.

Anal. Calcd. for C$_{18}$H$_{14}$F$_3$N$_3$O$_3$S: C, 52.81; H, 3.45; N, 10.26; S, 7.83.

Found: C, 52.73; H, 3.38; N, 10.44; S, 7.89.

Example 5

2-[Benzyl(methyl)amino]-8-nitro-6-(trifluoromethyl)-4H-1,3-benzothiazin-4-one, (compound 5)

Following the procedure of Example 4. Light yellow crystalline solid. Yield 47%. mp 120-124° C. (EtOH/water).

MS m/z 395 (M$^+$).

$^1$H NMR (DMSO-d$_6$/CDCl$_3$) δ 8.81 and 8.77 (two 1H, two s, 2CH), 7.40-7.25 (5H, m, C$_6$H$_5$), 4.64 (2H, s, CH$_2$), 2.87 (3H, s, CH$_3$) ppm.

Anal. Calcd. for C$_{17}$H$_{12}$F$_3$N$_3$O$_3$S: C, 51.64; H, 3.06; N, 10.63; S, 8.11.

Found: C, 51.76; H, 3.13; N, 10.41; S, 8.34.

Example 6

2-[4-(2-Fluorophenyl)piperazin-1-yl]-8-nitro-6-(trifluoromethyl)-4H-1,3-benzothiazin-4-one, (compound 6)

Following the procedure of Example 1. Light yellow crystalline solid. Yield 37%. mp 164-168° C. (i-PrOH).

MS m/z 454 (M$^+$).

$^1$H NMR (DMSO-d$_6$/CDCl$_3$) δ 8.81 and 8.77 (two 1H, two s, 2CH), 6.76 (3H, m, 3CH), 6.11 (1H, m, CH), 3.68 and 3.30 (two 4H, m, N(CH$_2$CH$_2$)$_2$N) ppm.

Anal. Calcd. for C$_{19}$H$_{14}$F$_4$N$_4$O$_3$S: C, 50.22; H, 3.11; N, 12.33; S, 7.06.

Found: C, 50.08; H, 3.21; N, 12.46; S, 7.09.

Example 7

2-(4-Benzylpiperazin-1-yl)-8-nitro-6-(trifluoromethyl)-4H-1,3-benzothiazin-4-one, (compound 7)

Following the procedure of Example 4. Yellow crystalline solid. Yield 51%. mp 161-163° C. (EtOH/DMF).

MS m/z 450 (M$^+$).

$^1$H NMR (DMSO-d$_6$/CDCl$_3$) δ 8.80 and 8.76 (two 1H, two s, 2CH), 7.19-7.28 (5H, m, Ph), 3.48 (2H, s, CH$_2$), 3.38 and 3.09 (two 4H, m, N(CH$_2$CH$_2$)$_2$N) ppm.

Anal. Calcd. for C$_{17}$H$_{18}$N$_4$O$_7$S: C, 53.33; H, 3.80; N, 12.44; S, 7.12.

Found: C, 53.29; H, 4.01; N, 12.48; S, 7.06.

Example 8

2-(Benzylamino)-8-nitro-6-(trifluoromethyl)-4H-1,3-benzothiazin-4-one, (compound 8)

A suspension of 2.5 g 2-chloro-3-nitro-5-trifluoromethylbenzcarboxamide in 25 ml ethanol was treated with of 1.75 g of sodium ethylxantogenate and stored for 24 h at room temperature. The reaction mixture was poured into 50 ml of cooled water and the resulting yellow precipitate was filtered off. Pure 2-ethoxy-8-nitro-6-(trifluoromethyl)-4H-1,3-benzothiazin-4-one was obtained after recrystallization from ethanol/water as white crystalline solid. Yield 58%. mp 146-148° C.

MS m/z 320 (M$^+$).

Anal. Calcd. for C$_{11}$H$_7$F$_3$N$_2$O$_4$S: C, 41.26; H, 2.20; N, 8.75; S, 10.01.

Found: C, 41.34; H, 2.22; N, 8.87; S, 10.27.

A solution of 0.7 g of 2-ethoxy-8-nitro-6-(trifluoromethyl)-4H-1,3-benzothiazin-4-one in 15 ml acetic acid was treated with 0.4 ml of benzylamine and refluxed for 14 h. The reaction mixture was evaporated and the residue was treated by 10 ml water, the yellow precipitate was filtered off and washed with 50 ml water. Pure final product was obtained after recrystallization twice from ethanol/DMF. 2-(Benzylamino)-8-nitro-6-(trifluoromethyl)-4H-1,3-benzothiazin-4-one is a light yellow crystalline solid. Yield 73%. mp 192-194° C.

MS m/z 381 (M$^+$).

$^1$H NMR (DMSO-d$_6$/CDCl$_3$) δ 9.27 (1H, broad s, NH), 8.80 and 8.75 (two 1H, two s, 2CH), 7.74-7.49 (5H, m, Ph), 4.49 (2H, s, CH$_2$) ppm. Anal. Calcd. for C$_{16}$H$_{10}$F$_3$N$_3$O$_3$S: C, 50.39; H, 2.64; N, 11.02; S, 8.41.

Found: C, 50.42; H, 2.61; N, 10.89; S, 8.64.

Example 9

2-{Methyl[(1R)-1-phenyl ethyl]amino}-8-nitro-6-(trifluoromethyl)-4H-1,3-benzothiazin-4-one, (compound 9)

Following the procedure of Example 1. Light yellow crystalline solid. Yield 54%. mp 110-113° C. (purification by column chromatography aceton/hexane 5:1).

MS m/z 409 (M$^4$).

$^1$H NMR (DMSO-d$_6$/CDCl$_3$) δ 8.82 and 8.76 (two 1H, two s, 2CH), 7.84, 7.43, 7.15 (5H, 3 m, Ph), 4.84 (H, m, CH), 3.07 (3H, s, NCH$_3$), 1.39 (3H, d, CH$_3$) ppm.

Anal. Calcd. for C$_{18}$H$_{14}$F$_3$N$_3$O$_3$S: C, 52.81; H, 3.45; N, 10.26; S, 7.83.

Found: C, 52.73; H, 3.46; N, 10.19; S, 7.92.

Example 10

2-[Benzyl(methyl)amino]-6-chloro-8-nitro-4H-1,3-benzothiazin-4-one, (compound 10)

Following the procedure of Example 8. Light yellow crystalline solid. Yield 64%. mp 138-141° C. (purification by column chromatography aceton/hexane 4:1).

MS m/z 361 (M$^+$).

$^1$H NMR (DMSO-d$_6$/CDCl$_3$) δ 8.37 and 8.23 (two 1H, two s, 2CH), 7.45-7.35 (5H, m, Ph), 4.62 (2H, 2, CH$_2$), 2.87 (3H, s, CH$_3$) ppm.

Anal. Calcd. for C$_{16}$H$_{12}$ClN$_3$O$_3$S: C, 53.11; H, 3.34; N, 11.61; S, 8.86.

Found: C, 53.19; H, 3.30; N, 11.52; S, 8.89.

Example 11

Determination of the in vitro inhibitory activity of the compounds of the invention against mycobacteria.

The antibacterial activities of the compounds against *Mycobacterium smegmatis* SG 987, *M. aurum* SB66, *M. vaccae* IMET 10670 and *M. fortuitum* B were tested by determination of minimal inhibitory concentrations (MIC) by the broth micro dilution method in Mueller-Hinton broth (Difco) according to the NCCLS guidelines [National Committee for Clinical Laboratory Standards: Methods for dilution antimicrobial susceptibility tests for bacteria that grow aerobically; 5$^{th}$ Ed.; Villanova, Ed.; Approved standard Document M7-A5. NCCLS, (2000)]. The results are presented in Table 1.

TABLE 1

Antimicrobial activity of compounds as of the formula I determined by minimal inhibitory concentrations MIC [μg/ml]

| Compound | *M. smegmatis* MIC [μg/ml] | *M. vaccae* MIC [μg/ml] | *M. fortuitum* MIC [μg/ml] |
|---|---|---|---|
| 1 | 0.78 | 0.0062 | 0.78 |
| 2 | 0.05 | 0.008 | 0.031 |
| 3 | 0.04 | 0.0031 | 0.0031 |
| 4 | 0.0062 | 0.0008 | 0.0062 |
| 5 | 0.0156 | 0.0005 | 0.0156 |
| 6 | 0.005 | 0.005 | 0.005 |
| 7 | 0.05 | 0.05 | 0.05 |
| 8 | 0.00078 | <0.0000121 | 0.00078 |
| 9 | <0.0000121 | <0.0000121 | <0.0000121 |
| 10 | 0.0062 | 0.00031 | 0.00156 |

Example 12

Activity against *M. tuberculosis* H37Rv was tested by the following method for determination of minimal inhibitory concentrations (MIC) and minimal bactericidal concentrations (MBC):

Strains were inoculated onto solid Lowenstein-Jensen medium. After 21 days, the cultures grown were used to prepare an inoculum suspension corresponding to 5×10$^8$ microbial cells/ml. With 0.2 ml of that suspension tubes with 2 ml liquid Shkolnikova medium, containing corresponding concentrations of compounds under study—from 100.0 to 0.195 μg/ml, were inoculated. After 14 days of incubation at 37° C. the tubes with liquid medium were centrifuged for 15 min. at 3000 RPM. After discarding the supernatant, the sediment was resuspended in 0.8 ml of sterile 0.9% NaCl. 0.1 ml of the suspension was used to prepare smears subsequently stained by the Ziehl-Neelsen method. The remaining sediment was inoculated in 0.2 ml volumes into three tubes with solid drug free Lowenstein-Jensen medium to determine minimal bactericidal concentrations (MBC). The results were read after 21-28 days of cultivation at 37° C. Controls were tubes cultured with test-strains not treated with the studied agents.

Minimal bactericidal concentration of drugs (MBC) was considered as the drug concentration completely inhibiting the growth of mycobacteria on the solid medium. The bacteriostatic effect (MIC) was characterized by the presence of only individual mycobacteria in the smear and a to strong decrease in the number of colonies grown on solid media compared to the controls. The results are presented in Table 2.

TABLE 2

Antimicrobial activity of compounds of the formula I against *Mycobacterium tuberculosis* H37Rv and clinical isolates HSRE resistant strain and XTB strain as determined by minimal inhibitory concentrations (MIC) and minimal bactericidal concentrations (MBC)

| Strain | Compound | MBC (μg/mL) | MIC (μg/mL) |
|---|---|---|---|
| H37Rv | 5 | 3.12 | 1.56 |
| HSRE resistant | | 3.12 | 1.56 |
| X TB | | 3.12 | 1.56 |
| H37Rv | 8 | 1.56 | 1.56 |
| HSRE resistant | | 1.56 | 0.78 |
| X TB | | 1.56 | 0.78 |
| H37Rv | 10 | 0.78 | <0.39 |
| HSRE resistant | | 1.56 | 1.56 |
| X TB | | 0.39 | <0.39 |
| H37Rv | Isoniazid (INH) | 1.56 | 0.78 |
| HSRE resistant | | Not active | |
| X TB | | Not active | |

HSRE: multiresistant strain
XTB: extremly resistant strain

Example 13

Activity against *M. tuberculosis* H37Rv was determined by the resazurin reduction assay (MIC$_{96}$) too. The method was described in detail in: P. Quillardet, O. Huisman, R. D'Ari, M. Hofnung, *Proc. Natl. Acad. Sci. USA,* 1982, 79, 5971-5; J. C. Palomino, A. Martin, M. Camacho, H. Guerra, J. Swings, F. Portaels, *Antimicrob. Agents Chemother.,* 2002, 46, 2720-2. The results are presented in Table 3.

TABLE 3

Antimycobacterial activity of compounds as of the formula I determined by minimal inhibitory concentrations (MIC) [ng/ml]

| Compound | *M. tuberculosis* H37Rv (ng/ml) |
|---|---|
| 4 | 2 |
| 5 | 3 |
| 8 | 50 |
| 9 | 0.4 |
| 10 | 25 |
| INH | 125 |

The invention claimed is:
1. A compound of formula (I)

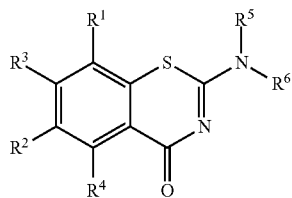

or a salt thereof,
wherein $R^1$ is $NO_2$;
$R^2$ is $NO_2$, a mono-, di- or trifluorinated methyl, Cl, F or Br;
$R^3$ and $R^4$ are independently from each other H or a saturated or unsaturated, linear or branched aliphatic radical having 1-3 chain members;
$R^5$ is H, a saturated or unsaturated, halogenated or unhalogenated, linear or branched aliphatic radical having 1-7 chain members;
$R^6$ is a radical:

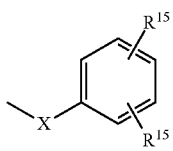

wherein X is a saturated or unsaturated, halogenated or unhalogenated, linear or branched aliphatic radical having 1-5 chain members, and;
$R^{14}$ and $R^{15}$ are, independently from each other H or a linear or branched aliphatic radical having 1-5 chain members.

2. A compound according to formula (I) of claim 1, selected from the group consisting of:
2-[Benzyl(methyl)amino]-8-nitro-6-$R^2$-4H-1,3-benzothiazin-4-one, wherein $R^2$ represents $CF_3$, Cl or F,
2-[Benzyl($R^5$)amino]-8-$R^1$-6-(trifluoromethyl)-4H-1,3-benzothiazin-4-one, wherein $R^1$ and $R^5$ have the same meaning as defined in claim 1.
6-$R^2$-2-[Methyl(2-phenylethyl)amino]-8-nitro-4H-1,3-benzothiazin-4-one, wherein $R^2$ has the same meaning as defined in claim 1,
6-Trifluoromethyl-2-[methyl(phenylethyl)amino]-8-$R^1$-4H-1,3-benzothiazin-4-one, wherein $R^1$ has the same meaning as defined in claim 1,
2-[Benzyl($R^5$)amino]-8-nitro-6-(trifluoromethyl)-4H-1,3-benzothiazin-4-one, wherein $R^5$ has the same meaning as defined in claim 1,
2-[Benzyl($R^5$)amino]-8-nitro-6-$R^2$-4H-1,3-benzozthiazin-4-one, wherein $R^2$ and $R^5$ have the same meaning as defined in claim 1,
2-[Benzyl($R^5$)amino]-8-nitro-6-chloro-4H-1,3-benzothiazin-4-one, wherein $R^5$ has the same meaning as defined in claim 1,
2-[Benzyl($R^5$)amino]-8-nitro-6-fluoro-4H-1,3-benzothiazin-4-one according to formula (I) of claim 1, wherein $R^5$ has the same meaning as defined in claim 1,
or a salt thereof.

3. A compound according to formula (I) of claim 1, selected from the group consisting of:
2-{Methyl[(1R)-1-phenylethyl)amino}-8-nitro-6-(trifluoromethyl)-4H-1,3-benzothiazin-4-one,
2-[Benzyl(ethyl)amino]-8-nitro-6-(trifluoromethyl)-4H-1,3-benzothiazin-4-one,
2-[Benzyl(methyl)amino]-8-nitro-6-(trifluoromethyl)-4H-1,3-benzothiazin-4-one,
2-(Benzylamino)-8-nitro-6-(trifluoromethyl)-4H-1,3-benzothiazine-4-one, and
2-[Benzyl(methyl)amino]-6-chloro-8-nitro-4H-1,3-benzothiazine-4-one,
or a salt thereof.

4. A pharmaceutical composition comprising a compound of formula (I) of any of claim 1, 2 or 3 or a salt thereof.

5. A medicament for the therapeutic treatment of bacterial infection in mammals comprising an effective amount of a compound of formula (I) of any of claim 1, 2 or 3 or a salt thereof.

6. A medicament according to claim 5, wherein the bacterial infection in mammals is a tuberculosis or leprosy infection.

7. A pharmaceutical composition comprising a compound of any of claim 1, 2 or 3 or a salt thereof.

8. A method of therapeutically or prophylactically treating a bacterial infection in mammals comprising administering to a mammal in need of such treatment the medicament of claim 5.

9. A method of therapeutically treating a tuberculosis or leprosy infection in mammals comprising administering to a mammal in need of such treatment the medicament of claim 5.

10. A method for the preparation of 2-$NR^5R^6$-4H1,3-benzothiazin-4-ones according to formula (I) of claim 1, comprising reacting 2-chlorobenzcarboxamides with 1.1 to 2.5 times in excess of metal salts of alkylxanthogenate at a temperature of 20-100° C. in a solvent and subsequently treating the resulting 2-alkoxy-4H-1,3-benzothiazin-4-one with an amine $HNR^5R^6$ in a solvent at a temperature of 20-100° C.

* * * * *

UNITED STATES PATENT AND TRADEMARK OFFICE
CERTIFICATE OF CORRECTION

PATENT NO.       : 8,440,842 B2
APPLICATION NO.  : 12/669748
DATED            : May 14, 2013
INVENTOR(S)      : Moellmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this
Eighth Day of September, 2015

Michelle K. Lee
*Director of the United States Patent and Trademark Office*